United States Patent [19]

Kimura et al.

[11] Patent Number: 5,274,187
[45] Date of Patent: Dec. 28, 1993

[54] PROCESS FOR PRODUCING COMPOUND HAVING CARBONYL AND/OR CARBOXYL GROUP

[75] Inventors: Hiroshi Kimura; Keiichi Tsuto, both of Wakayama, Japan

[73] Assignee: Kao Corporation, Tokyo, Japan

[21] Appl. No.: 936,666

[22] Filed: Aug. 28, 1992

[30] Foreign Application Priority Data

Aug. 30, 1991 [JP] Japan .................. 3-219760
Aug. 30, 1991 [JP] Japan .................. 3-219761

[51] Int. Cl.$^5$ .............................. C07C 51/16
[52] U.S. Cl. ........................ 562/538; 568/471
[58] Field of Search .................. 562/538; 568/471

[56] References Cited

U.S. PATENT DOCUMENTS 4,816,603  3/1989  Oh-Kita et al. .................. 562/538

Primary Examiner—Arthur C. Prescott
Attorney, Agent, or Firm—Birch, Stewart, Kolasch & Birch

[57] ABSTRACT

A compound having a carbonyl group and/or a carboxyl group is produced by catalytically oxidizing a polyhydric alcohol having at least one primary hydroxyl group and at least one secondary hydroxyl group in the presence of a supported catalyst comprising at least one catalytic component selected from among the following components (I) to (IV) loaded on a support:

(I) A first catalytic component chosen from at least one element selected from group A consisting of platinum, palladium, rhodium, ruthenium, rhenium, gold, silver and copper, (II) a combination of the first catalytic component with a second catalytic component chosen from at least one element selected from group B consisting of tin, lead, antimony, bismuth, selenium and tellurium, (III) a combination of the first catalytic component with a third catalytic component chosen from at least one element selected from group C consisting of rare earth elements, and (IV) a combination of the first catalytic component with the second catalytic component and the third catalytic component.

21 Claims, No Drawings

PROCESS FOR PRODUCING COMPOUND HAVING CARBONYL AND/OR CARBOXYL GROUP

BACKGROUND OF THE INVENTION

1. Field of the Invention

The present invention relates to a process for efficiently producing a compound having a carbonyl group and/or a carboxyl group (hereinafter referred to simply as "the carbonyl compound") useful as an important intermediate for physiologically active substances and amino acids from an inexpensive polyhydric alcohol.

2. Description of the Related Art

The carbonyl compounds including dihydroxyacetone (and its dimer), hydroxypyruvic acid, hydroxyacetone, pyruvic acid, glyceraldehyde (and its dimer), hydroxymalonic acid, glyceric acid, and lactic acid are very important intermediates for physiologically active substances and amino acids. As judged from the fundamental skeletons of these intermediates, it is conceivable that they may be derived from compounds having a secondary hydroxyl group, such as glycerol, 1,2-propylene glycol or derivatives of them.

Various processes have been proposed heretofore for deriving oxidized glycerol from glycerol by oxidation. For example, J. Org. Chem., 52, 2318 (1987) describes that glyceric acid is derived from glycerol by oxidation with nitric acid or mercury. However, this process is undesirable from the viewpoints of environmental pollution and waste water treatment. Further, although a process for producing glyceraldehyde by the electrolytic oxidation of glycerol is disclosed in British Patent No. 1051614, the concentration of the starting material, i.e., glycerol is too low for the practical application.

A process for producing dihydroxyacetone by oxidizing the secondary hydroxyl group of glycerol by an enzymatic reaction with Acetobacter sp. has been known. In addition, Japanese Patent Laid-Open No. 207255/1989 proposes a process for chemically synthesizing dihydroxyacetone by oxidizing glycerol with peracetic acid in an organic solvent. However, these microbial process and chemical synthesis process have problems in practice, since the yield is low and the concentration of the obtained dihydroxyacetone is low.

On the other hand, pyruvic acid is produced by the gas phase oxidation of lactic acid.

It is known that the oxidation products and dimers of them produced by the above-described conventional processes are thermally unstable and easily isomerized by a pH change. Therefore, these oxidation products or their dimers must be synthesized under mild conditions which are strictly controlled. However, the reactions conducted under the mild conditions have a defect that they take a long time. In the above-described conventional processes, the reaction must be conducted while the concentration is kept low in order to relax the inhibition of the reaction by the molecular association of the starting polyhydric alcohol and, in addition, these processes are unsatisfactory also from the viewpoint of the productivity.

DISCLOSURE OF THE INVENTION

Summary of the Invention

After extensive investigations made for the purpose of developing a high-productivity process for efficiently producing the carbonyl compound from a corresponding polyhydric alcohol by catalytic oxidation, namely, a process which satisfies a requirement that the intended compound can be obtained at a high concentration in a high yield at a high reaction velocity while by-products are formed in only small amounts, the inventors have found that the above-described problems can be solved by using a specified catalyst composition and a specified catalyst support. The present invention has been completed on the basis of this finding.

Namely, the present invention provides a process for producing the carbonyl compound, characterized by catalytically oxidizing a polyhydric alcohol having at least one primary hydroxyl group and at least one secondary hydroxyl group in the presence of a supported catalyst comprising at least one catalytic component selected from the following components (I) to (IV) supported by a support:

(I) at least one element selected from group A consisting of platinum, palladium, rhodium, ruthenium, rhenium, gold, silver and copper (hereinafter referred to as "the first catalytic component") alone, (II) a combination of the first catalytic component with at least one element selected from group B consisting of tin, lead, antimony, bismuth, selenium and tellurium (hereinafter referred to as "the second catalytic component"), (III) a combination of the first catalytic component with at least one element selected from group C consisting of rare earth elements (hereinafter referred to as "the third catalytic component"), and (IV) a combination of the first catalytic component with the second catalytic component and the third catalytic component.

The support is preferably at least one substance selected from the group consisting of active carbon, carbon black, silica, alumina, silica/alumina, zeolite, molecular sieve and asbestos.

The support is preferably active carbon and/or carbon black having at least one of the following properties (a) to (d) and an ash content of 15% by weight or below:

(a) a specific surface area of the active carbon and/or carbon black of at least 500 $m^2/g$,
(b) a bulk density of the active carbon and.or carbon black of 800 g/l or below,
(c) a pore volume of the active carbon and/or carbon black of at least 0.3 ml/g, and
(d) an average pore diameter of the active carbon and/or carbon black of 20 nm or below.

The process of the present invention is preferably conducted by using a fixed-bed reactor having a reaction column containing the supported catalyst fixed therein wherein liquid and gas phases are to be continuously flowed over the catalyst, and supplying oxygen gas or an oxygen-containing gas and the polyhydric alcohol in a molar ratio of the oxygen to the polyhydric alcohol of 0.1:1 to 100:1.

Further scope and the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The polyhydric alcohols usable as the starting material in the present invention are those having at least one primary hydroxyl group and at least one secondary hydroxyl group, such as glycerol, substituted glycerol, 1,2-propylene glycol, substituted 1,2-propylene glycol, glucose, substituted glucose, and sorbitol. Particularly effective starting materials in the present invention are glycerol and/or 1,2-propylene glycol.

The carbonyl compounds produced by the process of the present invention include dihydroxyacetone, hydroxyacetone, hydroxypyruvic acid, glyceraldehyde, glyceric acid, pyruvic acid, hydroxymalonic acid, lactic acid and mixtures of two or more of them.

Examples of the oxidizing agent usable in the present invention include oxygen gas, air and a gaseous mixture of oxygen and nitrogen having any desired composition, among which air is economically advantageous.

The catalytic components usable in the present invention include the first catalytic component (at least one element selected from the group consisting of platinum, palladium, rhodium, ruthenium, rhenium, gold, silver and copper), the second catalytic component (at least one element selected from the group consisting of tin, lead, antimony, bismuth, selenium and tellurium) and the third catalytic component (at least one element selected from the group consisting of rare earth elements). The catalyst comprises any of (I) the first catalytic component alone, (II) a combination of the first catalytic component with the second catalytic component, (III) a combination of the first catalytic component with the third catalytic component and (IV) a combination of the first catalytic component with the second catalytic component and the third catalytic component.

Platinum, palladium, silver, gold and copper are particularly effectively usable as the first catalytic component. Lead, bismuth, selenium and tellurium are effectively usable as the second component. Cerium and lanthanum are effectively usable as the third component. The elements selected from each group as the catalytic component may be used either singly or in combination of two or more of them. When two or more elements are selected from each group and used together, synergistic effects may be exhibited in some cases.

In practicing the present invention, the combination of the catalytic components is suitably selected from the above-described combinations (I) to (IV) depending on the site (primary or secondary hydroxyl group) of the polyhydric alcohol to be oxidized. For example, when mainly the primary hydroxyl group of the polyhydric alcohol is to be oxidized to form a carboxyl group, the combination (I) or (III) is preferred but when the poisoning of the catalyst by oxygen is serious, the combination (II) or (IV) can be employed. When mainly the secondary hydroxyl group of the polyhydric alcohol is to be oxidized, the combination (II) or (IV) is preferred.

The support for the supported catalyst to be used in the present invention is an ordinary support such as active carbon, carbon black, silica, alumina, silica/alumina, zeolite, molecular sieve and asbestos, among which active carbon and carbon black are advantageous.

When active carbon and/or carbon black are (is) to be used, those having at least one of the following properties (a) to (d) and an ash content of 15% by weight or below are particularly desirable:
(a) a specific surface area of the active carbon and/or carbon black of at least 500 $m^2/g$,
(b) a bulk density of the active carbon and/or carbon black of 800 g/l or below,
(c) a pore volume of the active carbon and/or carbon black of at least 0.3 ml/g, and
(d) an average pore diameter of the active carbon and/or carbon black of 20 nm or below.

The specific surface area of the support exerts a great influence on the dispersibility of the catalytic component. To obtain a high dispersibility, the specific surface area must be at least 500 $m^2/g$. When the specific surface area is below 500 $m^2/g$, the reaction of the present invention cannot be efficiently conducted. It is preferably at least 800 $m^2/g$, still preferably at least 1000 $m^2/g$ and particularly at least 1200 $m^2/g$. The bulk density of the support is very important in the properties of the support. The bulk density must be 800 g/l or below. When it is higher than this value, the reaction efficiency per unit weight of the catalytic component is seriously lowered. It is preferably 600 g/l or below, still preferably 400 g/l or below and particularly 200 g/l or below. The pore volume of the support must be at least 0.3 ml/g. When it is below this value, the reaction of the present invention does not efficiently proceed. It is preferably 0.6 ml/g or above, still preferably 0.9 ml/g or above and particularly 1.1 ml/g or above. The average pore diameter of the support must be 20 nm or below. When it is above this value, the catalytic activity is seriously lowered. It is preferably 10 nm or below, still preferably 6 nm or below and particularly 4 nm or below. The ash content of the support must be 15% by weight or below. When it exceeds this value, the catalytic activity might be lowered. It is preferably 5% by weight or below and still preferably 2% by weight or below. However, a support containing a heavy metal such as iron, nickel, cobalt, chromium or manganese in the ash is not preferred even when it has a low ash content, since such a heavy metal will exert a serious influence on the catalytic activity in the catalytic oxidation of the polyhydric alcohol to form the carbonyl compound. Therefore the contamination with the heavy metals is desirably inhibited to keep the heavy metal content on an as low as possible level.

The active carbon to be used as the catalyst support in the present invention can be produced from any of the starting materials such as coconut shell, wood, coal, peat and petroleum pitch. Among them, the active carbon obtained from coconut shell or petroleum pitch having a low ignition residue or ash content are particularly effective. An active carbon activated with steam or a chemical can be used. Among them, an active carbon activated with a chemical having a high activating effect is more effective in some cases. A commercially available active carbon can be used as it is or it can be subjected to a suitable pretreatment such as an acid treatment to regulate the pore distribution or to reduce the ash content prior to use. Examples of the commercially available active carbons in granular or powdery form include those usually used for treating water or refining water-soluble foods, such as powdery active carbons, represented by those of granular Shirasagi series (WH, Sx and KL) and powdery active carbons such a Carboraffin mfd. by Takeda Chemical Industries, Ltd.; granular active carbons (ROX, RAX, DARCO, C, ELORIT, etc.) and powdery active carbons (AZO, PN, ZN, etc.) mfd. by NORIT Co., Ltd.; and bead-shaped active carbon (BAC) mfd. by Kureha Chemical Industry Co., Ltd.

Commercially available carbon blacks are also usable as the catalyst support in conducting the reaction of the present invention. They include, for example, carbon black mfd. by Kyaburakku Co., Ltd.

The active carbons and carbon blacks usable in the present invention are, however, not limited to those described above as a matter of course.

The supported catalyst to be used in the present invention is produced by loading the first catalytic component on the support or loading the above-described catalytic components at once or stepwise on the support. The supported catalyst thus produced is activated with a reducing agent such as formaldehyde, hydrazine, sodium borohydride, hydrogen or methyl alcohol prior to use.

Commercially available platinum/carbon catalyst or palladium/carbon catalyst is also usable as the supported catalyst comprising the first catalytic component supported by the support. Further, the supported catalyst of the present invention can be produced by loading the second catalytic component and/or the third catalytic component on a commercially available platinum/carbon catalyst or palladium/carbon catalyst.

The supported catalyst to be used in the present invention may be a mixture of the first, second and third catalytic components each supported on a support such as granular active carbon, or alternatively all of these catalytic components supported on one and the same support.

The form of the supported catalyst is not particularly limited. It is suitably selected from among powder, granule and molding depending on the type of the reactor. When a fixed-bed reactor which will be described below in detail is used, a supported catalyst in the form of granule or molding is used.

The reaction path for the oxidation of the polyhydric alcohol according to the present invention will be described below with reference to glycerol and 1,2-propylene glycol as examples of the polyhydric alcohol.

Reaction Path for Oxidation of Glycerol

As shown in Scheme 1, the reaction path for the oxidation of glycerol includes a route via dihydroxyacetone wherein the secondary hydroxyl group is oxidized first and a route via glyceraldehyde wherein the primary hydroxyl group is oxidized first.

SCHEME 1

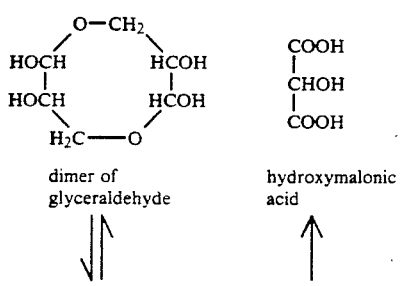

dimer of glyceraldehyde hydroxymalonic acid

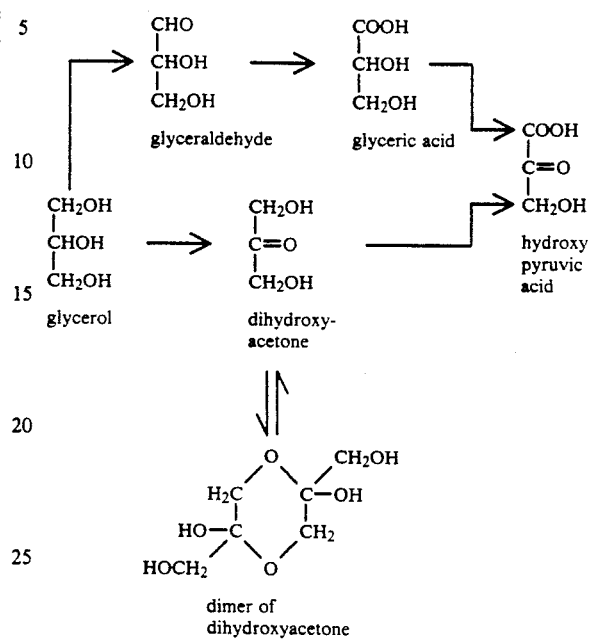

-continued
SCHEME 1

The route via dihydroxyacetone comprises the following two steps:
(1) oxidation of glycerol to form dihydroxyacetone, and
(2) oxidation of dihydroxyacetone to form hydroxypyruvic acid.

The route via glyceraldehyde comprises the following four steps:
(3) oxidation of glycerol to form glyceraldehyde,
(4) oxidation of glyceraldehyde to form glyceric acid,
(5) oxidation of glyceric acid to form hydroxypyruvic acid, and
(6) oxidation of glyceric acid to form hydroxymalonic acid.

Since each of the dihydroxyacetone and glyceraldehyde is present in the form of an equilibrium mixture thereof with its dimer in each of the above-described routes, the equilibrium is sifted to increase the monomers by controlling the concentration or pH.

Reaction Path for Oxidation of 1,2-Propylene Glycol

As shown in Scheme 2, also the reaction path for the oxidation of 1,2-propylene glycol includes a route via hydroxyacetone wherein the secondary hydroxyl group is oxidized first and a route via lactic acid wherein the primary hydroxyl group is oxidized first:

SCHEME 2

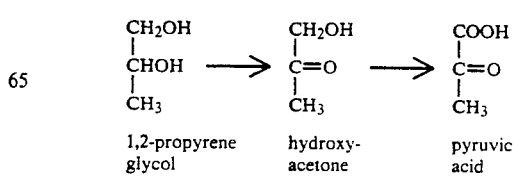

-continued
SCHEME 2

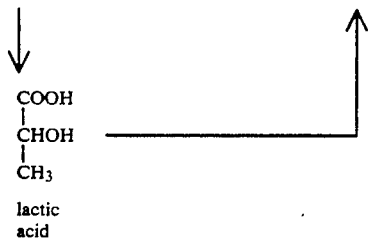

lactic
acid

The route via hydroxyacetone comprises the following two steps:
(7) oxidation of 1,2-propylene glycol to form hydroxyacetone, and
(8) oxidation of hydroxyacetone to form pyruvic acid.

The route via lactic acid comprises the following two steps:
(9) oxidation of 1,2-propylene glycol to form lactic acid, and
(10) oxidation of lactic acid to form pyruvic acid.

In synthesizing the intended product by any the above-described routes of the present invention, the reactions are preferably conducted under optimum conditions, which will be described below with reference to examples.

When dihydroxyacetone is to be produced from glycerol or hydroxyacetone is to be produced from 1,2-propylene glycol in the presence of the catalyst according to the present invention, the reaction temperature is desirably as low as possible. Namely, it ranges preferably $-20°$ to $60°$ C., still preferably $-10°$ to $60°$ C. and particularly $0°$ to $40°$ C. When the reaction temperature is above $60°$ C., the oxidation of the primary hydroxyl group is accelerated to lower the yields of dihydroxyacetone and hydroxyacetone. On the other hand, when it is below $-20°$ C., the reaction velocity is seriously lowered, which is not practical. The oxidation is desirably conducted in an acidic atmosphere. Therefore, the pH of the reaction system is maintained in the range of preferably 7 to 1, still preferably 6 to 2 and particularly 4 to 2. When an oxygen-containing gas is used as the oxidizing agent, the molar ratio of oxygen to the polyhydric alcohol is preferably 0.1:1 to 100:1, still preferably 0.25:1 to 30:1, particularly 0.5:1 to 10:1. When the molar ratio of the oxygen to the polyhydric alcohol is extremely large, the selectivity of the catalyst might be changed. The catalyst (II) or (IV) according to the present invention is preferably used.

In the production of glyceric acid or hydroxymalonic acid from glycerol via glyceraldehyde or in the production of lactic acid from 1,2-propylene glycol in the presence of the catalyst according to the present invention, the reaction temperature is preferably $0°$ to $80°$ C., still preferably $30°$ to $60°$ C. and particularly $30°$ to $50°$ C. In the oxidation of the primary hydroxyl group into a carboxyl group, it is preferred from the viewpoints of the reaction velocity and yield to conduct the oxidation in a basic atmosphere. This reaction is, therefore, conducted usually by adding an alkali. However, since an alkali metal salt of the carboxylic acid is formed by the oxidation conducted in a basic atmosphere, the neutralization step is necessitated for obtaining the carboxylic acid per se. When a catalytic element except for platinum is used as the catalytic element, the pH of the reaction system is adjusted to 7.5 to 13. When the catalytic element except for platinum is used, the oxidation is difficult to proceed in a neutral or an acidic atmosphere. As the catalytic element except for platinum, palladium is preferable. On the other hand, when platinum is used as the catalyst element, the reaction proceeds in either a basic or an acidic atmosphere favorably. Although a high reaction velocity can be obtained by the oxidation conducted in the presence of the platinum catalyst in a basic atmosphere of pH 7.5 or above, platinum is easily dissolved out in a basic atmosphere. Therefore, when platinum is used as the catalyst element, the pH is maintained in the range of preferably 7.5 to 1, still preferably 6 to 2 and particularly 4 to 2. Under these reaction conditions, the carboxylic acid per se can be advantageously produced without the necessity for the addition of any alkali to the reaction system. When an oxygen-containing gas is used as the oxidizing agent, the molar ratio of oxygen to the polyhydric alcohol is preferably 0.1:1 to 100:1, still preferably 0.5:1 to 20:1, particularly 1:1 to 5:1. The catalyst (I) according to the present invention is preferably used and the reaction velocity can be increased by using the rare earth element-containing catalyst (III). When the catalyst is seriously poisoned by oxygen, the catalyst (IV) is preferably used.

In the production of hydroxypyruvic acid from glyceric acid or dihydroxyacetone obtained from glycerol by the above oxidation process, the reaction temperature is preferably $30°$ to $60°$ C., the pH is preferably 3 to 6, the molar ratio of oxygen to the polyhydric alcohol is preferably 0.5 to 10 and the catalyst is preferably the catalyst (II) or (IV) according to the present invention.

In the production of glyceraldehyde from glycerol in the presence of the catalyst according to the present invention, preferred reaction temperature, pH and molar ratio of oxygen to the polyhydric alcohol are $0°$ to $40°$ C., 2 to 6 and 0.25:1 to 2:1, respectively, since glyceraldehyde is easily oxidized into glyceric acid, and the catalyst (I) is preferably used.

In the oxidation reaction of the polyhydric alcohol according to the present invention, the oxidations of the primary hydroxyl group and the secondary hydroxyl group proceed simultaneously. Therefore, the reaction system is to be acidic if an alkaline compound is not added thereto, because a carboxyl group is formed by the oxidation of the primary hydroxyl group. As described above, however, when an appropriate catalytic component is selected, and the reaction conditions, for example, pH, temperature and the molar ratio of the oxygen to the starting polyhydric alcohol, are maintained suitably, the selectivity for the oxidation reaction, i.e., either the primary hydroxyl group is oxidized or the secondary hydroxyl group is oxidized, can be controlled. As a result, a specified compound having a carbonyl group and/or a carboxyl group can be efficiently prepared.

Various carbonyl compounds are thus produced by the consecutive reactions from glycerol or 1,2-propylene glycol. When a specified carbonyl compound is to be produced, it will suffice when the reactions are conducted under such reaction conditions that the maximum concentration of the carbonyl compound will be obtained when empirically determined. However, the resulting oxidation product is in the form of a mixture, since the reactions are parallel and consecutive. The intended carbonyl compound is obtained, therefore, by conducting separation and purification by the usual methods such as chromatography, distillation and crystallization.

The reaction can be conducted either batchwise or continuously in the present invention. The reactor can be, for example, a mixing vessel, injecting, fluidized bed or fixed bed reactor.

A process for producing the carbonyl compound by using the fixed bed reactor, among others, having the following merits will be described in detail hereinbelow.

The carbonyl compounds produced by the reaction of the present invention are very important intermediates for physiologically active substances or amino acids as described above. Therefore, the carbonyl compound produced by the reaction of the present invention is often used as the starting material for other reaction(s). In this case, an additional step is necessitated for separating the catalyst used for the reaction of the present invention prior to the next reaction. Since, however, the catalyst separation step increases also process load particularly in the case of mass production, the use of the fixed bed reactor will bring about various merits in the productivity, such as dispensation with the catalyst separation step and capability of conducting the reaction with the starting materials at high concentrations.

For example, dihydroxyacetone which is one of the carbonyl compounds produced by the process of the present invention was produced for the first time in 1896 by fermentation and is still now produced by the same method. Therefore, the step of separating the microbes is indispensable and the reaction must be conducted for a long period of time by using the starting materials of low concentrations, so that an increase in the production efficiency is an important problem in this process. For solving this problem, the reaction of the present invention conducted in the fixed bed reactor is very advantageous.

Namely, the present invention makes it possible to prepare a granular catalyst for the fixed bed reactor by using various catalyst supports, packing the catalyst in the fixed bed reactor and catalytically oxidizing a polyhydric alcohol in the reactor to thereby form a carbonyl compound. As a result, objects of the present invention, i.e. (1) the performance of the reaction of an aqueous solution of the starting polyhydric alcohol having a high concentration (at least 20% by weight) and (2) the attainment of a high conversion and, in addition, (3) the dispensation with the step of separating the catalyst from the oxidation products have succeeded. Further the use of the fixed bed reactor contributes to a great improvement in the durability of the catalyst, since the deterioration of the catalyst due to the physical breakage thereof caused by stirring in a batchwise reactor is avoidable.

More specifically, for example, when a 50 wt. % aqueous solution of glycerol is catalytically oxidized with air or oxygen gas in an acidic atmosphere in a fixed bed reactor containing the catalytic component (II) or (IV) loaded on a support developed by the inventors, dihydroxyacetone which is an important intermediate for physiologically active substances or amino acids can be produced in a yield of about 80 molar %. Dihydroxyacetone has been heretofore produced by fermentation as described above and the process for producing dihydroxyacetone by the catalytic oxidation has not been known in the world prior to the present invention. The process of the present invention is thus very valuable.

When a 50 wt. % aqueous solution of 1,2-propylene glycol is subjected to the same reaction as that described above in the presence of the same catalyst as that described above, hydroxyacetone usable as an intermediate for amino acids can be obtained in a yield of about 80 molar %. When a 50 wt. % aqueous solution of glycerol is catalytically oxidized in the fixed bed reactor containing the catalytic component (I) or (III) loaded on the support in an acidic atmosphere, glyceric acid usable as an important intermediate can be obtained in a yield of 80 molar % or above, and when the oxidation is further continued, hydroxymalonic acid is obtained in a high yield.

It has been impossible heretofore to subject glycerol or 1,2-propylene glycol (polyhydric alcohol) in the form of its aqueous solution having a concentration of as high as 50% by weight to the liquid phase catalytic oxidation reaction. The use of the 50 wt. % aqueous solution of polyhydric alcohol is a characteristic feature of the catalytic oxidation process conducted in the presence of the high-concentration catalyst in the fixed bed reactor.

Another characteristic feature of the present invention wherein the fixed bed reactor is used is that not only the starting polyhydric alcohol having a high concentration can be subjected to the oxidation but also, surprisingly, the carbonyl compound can be obtained with a high selectivity and the step of separating the catalyst can be dispensed with. Thus the process of the present invention is a very excellent process for producing the carbonyl compounds usable as important intermediates for physiologically active substances and amino acids having a high value added from the inexpensive polyhydric alcohols.

The fixed bed reactor is, for example, one having a reaction column provided with an inlet for the starting material and oxidizing agent and an outlet for the reaction mixture, etc., and containing the supported catalyst packed therein.

In conducting the process of the present invention in the fixed bed reactor, the supported catalyst according to the present invention comprising the catalyst loaded on the support having a granule size of larger than 200 mesh is packed in the reaction column (packed column) so that the ratio (L/D) of the length (L) of the packed catalyst depth to the inner diameter (D) of the reaction column will be at least 1, preferably at least 5, still preferably at least 20, and then an aqueous polyhydric alcohol solution and oxygen gas or an oxygen-containing gas are introduced into the reaction column in a molar ratio of the oxygen to the polyhydric alcohol of 0.1:1 to 100:1 countercurrently or cocurrently. A reactor of trickle bed type wherein both of the aqueous polyhydric alcohol solution and oxygen gas or an oxygen-containing gas are cocurrently introduced downward through the top of the reaction column is particularly effective. The reaction pressure in the reaction column is usually 50 atm or below, preferably 10 atm or below and still preferably a atmospheric pressure. By continuously introducing the aqueous solution of the polyhydric alcohol as the starting material and oxygen gas or the oxygen-containing gas as the oxidizing agent over the supported catalyst (fixed bed), the oxidation product is continuously obtained in the form of a colorless transparent aqueous solution through the outlet of the reaction column.

It is desirable to provide liquid distributors having pores at the top and two or more other places of the reaction column, if necessary, since when the aqueous polyhydric alcohol solution and the reaction mixture (liquid phase) cause channelling flow in the reaction column, such a flow comes to exerts a significant influence on the oxidation.

When the oxidation is conducted in an acidic atmosphere as, for example, in the oxidation of the secondary hydroxyl group of the polyhydric alcohol, the inner wall of the reaction column must be made from an acid-resistant material from which no transition metal ion is leached. Namely, the leaching metal ions of the Group VIII elements of the periodic table, such as iron, cobalt, nickel, chromium and manganese ions might exert a great influence on the activity and selectivity of the catalyst especially in the oxidation of the secondary hydroxyl group of the polyhydric alcohol. In such a case, a glass-lined reactor comprising a reaction column having a glass-coated inner wall is preferably used.

The liquid hourly space velocity (LHSV) of the aqueous polyhydric alcohol solution to be introduced into the reaction column is preferably 0.01 to 5, still preferably 0.01 to 1.0. The LHSV is determined by the following formula:

$$LHSV = \frac{\text{aqueous polyhydric alcohol feed rate } [l/h]}{\text{volume of packed catalyst } [l]}$$

In the production of the carbonyl compounds by the catalytic oxidation of the primary hydroxyl group or secondary hydroxyl group of the polyhydric alcohol in the fixed bed reactor, the reaction conditions such as pH, temperature and molar ratio of oxygen to the polyhydric alcohol are as described above with reference to Schemes 1 and 2.

An embodiment of the method for adjusting the pH of the reaction system is as follows:

When the reaction is conducted in an acidic atmosphepe, an acid is added to the reaction system.

When the reaction system is to be acidic because of the formation of a carboxyl group which derives a parallel reaction, none is added to the reaction system for the reaction in an acidic atmosphere.

When the reaction is conducted in a basic atmosphepe, an aqueous alkali solution such as an aqueous sodium hydroxide solution is introduced through the top or an intermediate part of the reaction column in addition to the aqueous polyhydric alcohol solution and oxygen gas or the oxygen-containing gas.

The pH of the reaction system is adjusted by determing the pH of the reaction mixture which is sampled from the outlet for sampling which is provided on the way or intermediate of the longitudinal direction of the reaction column or the pH of the reaction mixture which is sampled from the outlet for the reaction product which is provided in the lower part of the reaction column. For example, when the primary hydroxyl group of the polyhydric alcohol is to be oxidized into a carboxyl group, the pH of the reaction mixture at the outlet of the reaction column is maintained at preferably 7.5 to 13, still preferably 8 to 11 and particularly 8 to 9 during the reaction. When the secondary hydroxyl group of the polyhydric alcohol is to be oxidized, the pH of the reaction mixture at the outlet of the reaction column is maintained at preferably 7 to 1, still preferably 6 to 2 and particularly 4 to 2 during the reaction so as to conduct the oxidation under an acidic condition.

As described above, the process of the present invention can be conducted by a method other than the fixed bed method. For example, when the reaction of the present invention is conducted batchwise in a stirred reactor, the aqueous polyhydric alcohol solution and the supported catalyst are fed into the reactor provided with a thermometer and a pH meter and having an air inlet, a exhaust gas outlet and a sampling port and an oxygen-containing gas is introduced into the reaction liquid under stirring at atmospheric pressure to conduct the catalytic oxidation of the polyhydric alcohol. After the completion of the reaction, the supported catalyst is separated by a known method (such as filtration) to obtain an aqueous solution containing the carbonyl compound.

The process of the present invention for producing the carbonyl compound allows a useful carbonyl compound of a high concentration to be efficiently produced from an inexpensive starting material by using the supported catalyst comprising the specified metallic catalyst and support.

In addition, the use of the fixed bed reactor makes it possible to conduct the reaction of the aqueous polyhydric alcohol solution having a concentration of as high as at least 20% by weight, to remarkably enhance the yield of the carbonyl compound, to dispense with the step of separating the catalyst, and to achieve high efficiency and productivity. Thus the pervasive effects achieved by the present invention are remarkable.

EXAMPLES

The following Examples will further illustrate the present invention, which by no means limit the invention.

The following Referential Examples will illustrate the preparation of the catalyst. In the Examples, the concentration of the product is given by molar %.

REFERENTIAL EXAMPLE 1

The catalyst was prepared by the following ordinary method: 67 g of commercially available granular wooden active carbon (100- to 40-mesh) activated with steam was immersed in a deionized water and a homogeneous aqueous solution of 5 g of chloroplatinic acid and 0.6 g of bismuth chloride in 12N-HCl was added thereto to load the catalytic components. The supported catalyst thus obtained was activated with a 35 wt. % aqueous formaldehyde solution (formalin) to obtain about 140 g of a catalyst comprising 0.6% of Bi and 3% of Pt supported on the active carbon having a water content of about 50%.

In Examples 1 through 14, the continuous oxidation of the polyhydric alcohol was conducted by the following fixed bed reaction method:

Fixed Bed Reaction Method 30 g (on dry basis) of the supported catalyst according to the present invention was packed in a Pyrex reactor having an inner diameter of 20 mm and a height of 70 cm to be a packing height of 60 cm. Both a 50 wt. % aqueous polyhydric alcohol solution and air (at atmospheric pressure) were continuously fed into the reactor downward through the top thereof. The liquid hourly space velocity (LHSV) of the aqueous polyhydric alcohol solution was 0.08 to 0.15 $h^{-1}$.

The resulting reaction mixture sampled from the outlet of the reactor was analyzed for the carbonyl compound by high-performance liquid chromatography (HPLC).

In Examples 15 to 19, the oxidation of the polyhydric alcohol was conducted batchwise by the following stirred tank reaction method:

Stirred Vessel Reaction Method 2.5 g (on dry basis) of the supported catalyst and 500 g of a 10 wt. % aqueous glycerol solution at 50° C. were fed into a 1-l flask provided with a temperature-regulating means, stirrer, air inlet, exhaust gas outlet, sample outlet and pH meter.

Then oxidation was conducted by introducing 6 l/h of air (at ambient temperature and atmospheric pressure) into the liquid at 50° C. for 6 h.

The supported catalyst was separated from the obtained reaction mixture by filtration and the carbonyl compound was analyzed by HPLC.

The conditions of the HPLC were as follows:

| high-performance liquid chromatograph: | |
| --- | --- |
| | D-2500/L-6000 type mfd. by Hitachi, Ltd., |
| detector: | L-3300 type (RI monitor), |
| column: | C-610S, |
| eluent: | 0.5 ml/min of distilled water, |
| pressure: | 15 kgf/cm$^2$, |
| temperature: | 60° C. |

The measurement of the pH of the reaction mixture sampled in fixed bed reaction method or stirred vessel reaction method was conducted as it is, i.e., not diluted.

EXAMPLE 1

A 50 wt. % aqueous glycerol solution was used as the polyhydric alcohol. The supported catalyst used comprised 0.6% of bismuth and 3% of platinum supported on an active carbon having an ash content of 2 wt. % or less and a specific surface area of 1500, 1000 or 700 m$^2$/g. Continuous oxidation was conducted according to the above-described fixed bed reaction method under the conditions comprising a reaction temperature of 50° C., a molar ratio of oxygen to polyhydric alcohol of 2:1, a pH of 4-2 and a LHSV of 0.08 h$^{-1}$.

The results are given in Table 1. It is apparent therefrom that the yield of dihydroxyacetone was increased as the specific surface area of the active carbon was increased.

The pH of the reaction mixture shown in Table 1 was one determined immediately after being discharged through the outlet for the reaction product of the reactor.

EXAMPLE 2

The oxidation was conducted under the same conditions as those of the Example 1 except that an active carbon having an ash content of 2 wt. % or less, a specific surface area of 1400 m$^2$/g and a bulk density of 170, 470 or 650 g/l was used as the catalyst support.

It was found that the active carbon having a bulk density of 500 g/l or below, particularly 200 g/l or below, was recommendable as the support, as shown in Table 1.

EXAMPLE 3

The oxidation was conducted under the same conditions as those of the Example 1 except that an active carbon having an ash content of 5 wt. % or less and a pore volume of 0.5, 0.8, 1.1 or 1.3 ml/g was used as the catalyst support.

It was found that the active carbon having a pore volume of at least 0.8 ml/g, particularly at least 1.3 ml/g, was recommendable as the support.

EXAMPLE 4

The oxidation was conducted under the same conditions as those of the Example 1 except that an active carbon having an ash content of 2 wt. % or less and an average pore diameter of 1.8, 3.5 or 12 nm was used as the catalyst support.

The results are given in Table 1.

EXAMPLE 5

The oxidation was conducted under the same conditions as those of the Example 1 except that an active carbon having a bulk density of 500 g/l less and an ash content of 13, 5 or 2 wt. % or an active carbon having an ash content of 1 wt. % which had been treated with nitric acid was used as the catalyst support.

The results are given in Table 1.

EXAMPLE 6

The oxidation was conducted under the same conditions as those of the Example 1 except that a supported catalyst prepared by loading 0.6% of bismuth and 3% of platinum on a granular active carbon (100- to 40-mesh) having a specific surface area of 1500 m$^2$/g, a pore volume of 1.3 ml/g, a bulk density of 170 g/l, an average pore diameter of 3.5 nm and an ash content of 2 wt. % was used; a 50% aqueous solution of 1,2-propylene glycol as a polyhydric alcohol having a secondary hydroxyl group was used as the starting material; and the liquid hourly space velocity was altered to 0.15 h$^{-1}$.

As a result, hydroxyacetone was produced in a yield of 78 molar % as given in Table 2.

EXAMPLE 7

A 3% platinum/carbon catalyst was prepared by using the same active carbon as that used in the Example 6 as the catalyst support and platinum alone [catalyst (I)] as the catalytic component. The oxidation was conducted under the same conditions as those of the Example 1 except that the 3% platinum/carbon catalyst thus prepared was used.

As a result, glyceric acid was produced in a yield of 85 molar % as given in Table 2.

EXAMPLE 8

The oxidation was conducted under the same conditions as those of the Example 7 except that a 20 wt. % aqueous sodium hydroxide solution was continuously introduced through an intermediate part of the reaction column at a rate of 15 molar % based on the feeding rate of glycerol and the liquid hourly space velocity of the aqueous glycerol solution was altered to 0.15 h$^{-1}$. After realizing a stationary state, the reaction mixture at the outlet of the reaction column was in the form of a colorless aqueous solution having a pH of 3. It comprised glyceric acid, hydroxymalonic acid and unreacted glycerol in amounts of 37 molar %, 49 molar % and 14 molar %, respectively.

EXAMPLE 9

The oxidation was conducted under the same conditions as those of the Example 1 except that the supported catalyst prepared in the Example 6 was used and the molar ratio of oxygen to glycerol was altered to 0.5, 2, 5, 10 or 30. The results are given in Table 2.

EXAMPLE 10

The oxidation was conducted under the same conditions as those of the Example 9 except that the molar ratio of oxygen to glycerol was altered to 2 and the pH of the reaction mixture at the outlet of the reaction column was adjusted to 9, 7, 5 or 2. The results are given in Table 2.

EXAMPLE 11

The oxidation was conducted under the same conditions as those of the Example 9 except that the molar ratio of oxygen to glycerol was altered to 2 and the reaction temperature was altered to −10°, 0°, 20°, 40°, 50°, 60° or 80° C. The results are given in Table 3.

EXAMPLE 12

The oxidation was conducted under the same conditions as those of Example 9 except that the molar ratio of oxygen to glycerol was altered to 2 and granular carbon black mfd. by Kyaburakku Co., Ltd. was used as the catalyst support. The yield of dihyroxyacetone was 78% as given in Table 3.

EXAMPLE 13

The oxidation was conducted under the same conditions as those of the Example 6 except that a 50% aqueous glycerol solution was used as the starting polyhydric alcohol and 1% Ce.5% Pt was used as the catalytic component. Glyceric acid was obtained in a yield of 88% as given in Table 3.

EXAMPLE 14

The oxidation was conducted under the same conditions as those of the Example 6 except that a 50% aqueous glycerol solution was used as the starting polyhydric alcohol and 1% Ce.1% Bi.5% Pt was used as the catalytic component. Dihydroxyacetone was obtained in a yield of 88% as given in Table 3.

EXAMPLE 15

A 5% Pt/carbon catalyst was prepared by using the same support as that described in the Example 6. The oxidation was conducted in the presence of that catalyst by the above-described stirred vessel reaction method. Glyceric acid and dihydroxyacetone were obtained in yields of 4% and 33%, respectively, as shown in Table 4.

EXAMPLE 16

The oxidation was conducted under the same conditions as those of the Example 15 except that 1% Bi.5% Pt was used as the catalytic component. The yields of glyceric acid and dihydroxyacetone were 5% and 25%, respectively, as given in Table 4.

EXAMPLE 17

The oxidation was conducted under the same conditions as those of the Example 15 except that 1% Ce.5% Pt was used as the catalytic component. The yields of glyceric acid and dihydroxyacetone were 83% and 7%, respectively, as given in Table 4.

EXAMPLE 18

The oxidation was conducted under the same conditions as those of the Example 15 except that 1% Ce.1% Bi.5% Pt was used as the catalytic component. The yields of glyceric acid and dihydroxyacetone were 15% and 74%, respectively, as given in Table 4.

EXAMPLE 19

The oxidation was conducted under the same conditions as those of the Example 16 except that asbestos, silica or alumina was used as the catalyst support. The results are given in Table 4.

TABLE 1

| Ex. No. | Starting polyhydric alcohol | Catalyst | Properties of the support | | | temp. | molar ratio of $O_2$ | pH | LHSV | Product (molar %) | Remarks |
|---|---|---|---|---|---|---|---|---|---|---|---|
| 1 | 50% glycerol | 0.6% Bi · 3% Pt, catalyst (II) | specific surface area of active carbon: | 1500 1000 700 | $m^2/g$ | 50° C. 50° C. 50° C. | 2 2 2 | 4~2 4~2 4~2 | 0.08 0.08 0.08 | DHA 75 DHA 50 DHA 32 | effect of specific surface area of active carbon, fixed bed reaction |
| 2 | 50% glycerol | 0.6% Bi · 3% Pt, catalyst (II) | bulk density of active carbon: | 170 470 650 | g/l | 50° C. 50° C. 50° C. | 2 2 2 | 4~2 4~2 4~2 | 0.08 0.08 0.08 | DHA 78 DHA 40 DHA 35 | effect of bulk density of active carbon, fixed bed reaction |
| 3 | 50% glycerol | 0.6% Bi · 3% Pt, catalyst (II) | pore volume of active carbon: | 0.5 0.8 1.1 1.3 | ml/g | 50° C. 50° C. 50° C. 50° C. | 2 2 2 2 | 4~2 4~2 4~2 4~2 | 0.08 0.08 0.08 0.08 | DHA 30 DHA 42 DHA 60 DHA 75 | effect of pore volume of active carbon, fixed bed reaction |
| 4 | 50% glycerol | 0.6% Bi · 3% Pt, catalyst (II) | average pore diameter of active carbon: | 1.8 3.5 12.0 | nm | 50° C. 50° C. 50° C. | 2 2 2 | 4~2 4~2 4~2 | 0.08 0.08 0.08 | DHA 70 DHA 80 DHA 67 | effect of average pore diameter of active carbon, fixed bed reaction |
| 5 | 50% glycerol | 0.6% Bi · 3% Pt, catalyst (II) | ash content of active carbon: | 12 5 2 1 | wt. % | 50° C. 50° C. 50° C. 50° C. | 2 2 2 2 | 4~2 4~2 4~2 4~2 | 0.08 0.08 0.08 0.08 | DHA 40 DHA 63 DHA 78 DHA 72 | effect of ash content, fixed bed reaction |

(Note)
DHA: dihydroxyacetone

TABLE 2

| Ex. No. | Starting polyhydric alcohol | Catalyst | Properties of the support | | temp. | molar ratio of $O_2$ | pH | LHSV | Product (molar %) | | Remarks |
|---|---|---|---|---|---|---|---|---|---|---|---|
| 6 | 50% propylene glycol | 0.6% Bi · 3% Pt, catalyst (II) | active carbon having: specific surface | 1500 $m^2/g$ | 50° C. | 2 | 4~2 | 0.15 | HA | 78 | oxidation of propylene glycol, fixed bed reaction |

TABLE 2-continued

| Ex. No. | Starting polyhydric alcohol | Catalyst | Properties of the support | | Reaction conditions | | | | Product (molar %) | | Remarks |
|---|---|---|---|---|---|---|---|---|---|---|---|
| | | | | | temp. | molar ratio of $O_2$ | pH | LHSV | | | |
| | | | area | | | | | | | | |
| | | | bulk density | 170 g/l | | | | | | | |
| | | | pore volume | 1.3 ml/g | | | | | | | |
| | | | average pore diameter | 3.5 nm | | | | | | | |
| | | | ash content | 2 wt. % | | | | | | | |
| 7 | 50% glycerol | 3% Pt, catalyst (I) | the same as in Ex. 6 | | 50° C. | 2 | 4~2 | 0.08 | GA | 85 | Pt/C catalyst, fixed bed reaction |
| 8 | 50% glycerol | 3% Pt, catalyst (I) | the same as in Ex. 6 | | 50° C. | 2 | 6~3 | 0.15 | GA OMA | 37 49 | effect of pH, fixed bed reaction |
| 9 | 50% glycerol | 0.6% Bi · 3% Pt, catalyst (II) | the same as in Ex. 6 | | 50° C. | 0.5 | 4~2 | 0.08 | DHA | 36 | effect of molar ratio of oxygen to the starting, polyhydric alcohol, fixed bed reaction |
| | | | | | 50° C. | 2 | 4~2 | 0.08 | DHA | 76 | |
| | | | | | 50° C. | 5 | 4~2 | 0.08 | DHA | 78 | |
| | | | | | 50° C. | 10 | 4~2 | 0.08 | DHA | 46 | |
| | | | | | 50° C. | 30 | 4~2 | 0.08 | DHA | 35 | |
| 10 | 50% glycerol | 0.6% Bi · 3% Pt, catalyst (II) | the same as in Ex. 6 | | 50° C. | 2 | 9 | 0.08 | DHA | 30 | effect of pH, fixed bed reaction |
| | | | | | 50° C. | 2 | 7 | 0.08 | DHA | 45 | |
| | | | | | 50° C. | 2 | 5 | 0.08 | DHA | 62 | |
| | | | | | 50° C. | 2 | 2 | 0.08 | DHA | 76 | |

(Notes)
HA: hydroxyacetone
GA: glyceric acid
OMA: hydroxymalonic acid
DHA: dihydroxyacetone

TABLE 3

| Ex. No. | Starting polyhydric alcohol | Catalyst | Properties of the support | Reaction conditions | | | | Product (molar %) | | Remarks |
|---|---|---|---|---|---|---|---|---|---|---|
| | | | | temp. | molar ratio of $O_2$ | pH | LHSV | | | |
| 11 | 50% glycerol | 0.6% Bi · 3% Pt, catalyst (II) | the same as in Ex. 6 | −10° C. | 2 | 4~2 | 0.08 | DHA | 42 | effect of temp, fixed bed reaction |
| | | | | 0° C. | 2 | 4~2 | 0.08 | DHA | 60 | |
| | | | | 20° C. | 2 | 4~2 | 0.08 | DHA | 70 | |
| | | | | 40° C. | 2 | 4~2 | 0.08 | DHA | 77 | |
| | | | | 50° C. | 2 | 4~2 | 0.08 | DHA | 76 | |
| | | | | 60° C. | 2 | 4~2 | 0.08 | DHA | 50 | |
| | | | | 80° C. | 2 | 4~2 | 0.08 | DHA | 23 | |
| 12 | 50% glycerol | 0.6% Bi · 3% Pt, catalyst (III) | granulated carbon black (mfd. by Kyaburakku Co., Ltd.) having: specific surface area 1000 m²/g; bulk density 300 g/l; pore volume 0.8 ml/g; average pore diameter 5 nm; ash content 0.5 wt. % | 50° C. | 2 | 4~2 | 0.08 | DHA | 78 | carbon black used, fixed bed reaction |
| 13 | 50% glycerol | 1% Ce · 5% Pt, catalyst (III) | the same as in Ex. 6 | 50° C. | 2 | 4~2 | 0.15 | GA | 88 | catalyst (III) used, fixed bed reaction |
| 14 | 50% glycerol | 1% Ce · 1% Bi · 5% Pt, catalyst (IV) | the same as in Ex. 6 | 50° C. | 2 | 4~2 | 0.15 | DHA | 88 | catalyst (IV) used, fixed bed reaction |

(Notes)
DHA: dihydroxyacetone
GA: glyceric acid

TABLE 4

| Ex. No. | Starting polyhydric alcohol | Catalyst | Properties of the support | Reaction conditions | | | | Product (molar %) | | Remarks |
|---|---|---|---|---|---|---|---|---|---|---|
| | | | | temp. | molar ratio of $O_2$ | pH | reaction time | | | |
| 15 | 10% glycerol | 5% Pt, catalyst (I) | the same as in Ex. 6 | 50° C. | 2 | 4~2 | 6 hr | DHA GA | 4 33 | catalyst (I) used, stirred vessel reaction |
| 16 | 10% glycerol | 1% Bi · 5% Pt, catalyst (III) | the same as in Ex. 6 | 50° C. | 2 | 4~2 | 6 hr | DHA GA | 25 5 | catalyst (II) used, stirred vessel reaction |
| 17 | 10% glycerol | 1% Ce · 5% Pt, catalyst (III) | the same as in Ex. 6 | 50° C. | 2 | 4~2 | 6 hr | DHA GA | 7 83 | catalyst (III) used, stirred vessel reaction |
| 18 | 10% glycerol | 1% Ce · 1% Bi · | the same as in Ex. 6 | 50° C. | 2 | 4~2 | 6 hr | DHA GA | 74 15 | catalyst (IV) used, stirred vessel reaction |

TABLE 4-continued

| Ex. No. | Starting polyhydric alcohol | Catalyst | Properties of the support | Reaction conditions | | | | Product (molar %) | | Remarks |
|---|---|---|---|---|---|---|---|---|---|---|
| | | | | temp. | molar ratio of $O_2$ | pH | reaction time | | | |
| 19 | 10% glycerol | 5% Pt, catalyst (IV) 1% Bi · 5% Pt, catalyst (II) | asbestos silica alumina | 50° C. 50° C. 50° C. | 2 2 2 | 4~2 4~2 4~2 | 6 hr 6 hr 6 hr | GA 10 6 4 | DHA 18 15 9 | effect of various carriers, stirred vessel reaction |

(Notes)
GA: glyceric acid
DHA: dihydroxyacetone

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for producing a compound having a carbonyl group and/or a carboxyl group, which comprises catalytically oxidizing a polyhydric alcohol having at least one primary hydroxyl group and at least one secondary hydroxyl group in the presence of a supported catalyst comprising at least one catalytic component selected from among the following components (I) to (IV) loaded on a support:
   (I) at least one element selected from group A consisting of platinum, palladium, rhodium, ruthenium, rhenium, gold, silver and copper (hereinafter referred to as "the first catalytic component") alone,
   (II) a combination of the first catalytic component with at least one element selected from group B consisting of tin, lead, antimony, bismuth, selenium and tellurium (hereinafter referred to as "the second catalytic component"),
   (III) a combination of the first catalytic component with at least one element selected from group C consisting of rare earth elements (hereinafter referred to as "the third catalytic component"), and
   (IV) a combination of the first catalytic component with the second catalytic component and the third catalytic component.

2. The process for producing a compound having a carbonyl group and/or a carboxyl group according to claim 1, wherein the support is at least one member selected from the group consisting of active carbon, carbon black, silica, alumina, silica/alumina, zeolite, molecular sieve and asbestos.

3. The process for producing a compound having a carbonyl group and/or a carboxyl group according to claim 1, wherein the support is active carbon and/or carbon black having at least one of the following properties (a) to (d) and an ash content of 15% by weight or below:
   (a) a specific surface area of the active carbon and/or carbon black of at least 500 m$^2$/g,
   (b) a bulk density of the active carbon and/or carbon black of 800 g/l or below,
   (c) a pore volume of the active carbon and/or carbon black of at least 0.3 ml/g, and
   (d) an average pore diameter of the active carbon and/or carbon black of 20 nm or below.

4. The process for producing a compound having a carbonyl group and/or a carboxyl group according to claim 1, wherein the catalytic oxidation is conducted by using oxygen gas, air or a gaseous mixture of nitrogen and oxygen.

5. The process for producing a compound having a carbonyl group and/or a carboxyl group according to claim 1, wherein the polyhydric alcohol is glycerol and/or 1,2-propylene glycol.

6. The process for producing a compound having a carbonyl group and/or a carboxyl group according to claim 1, wherein the compound having a carbonyl group and/or a carboxyl group is at least one compound selected from the group consisting of dihydroxyacetone, hydroxyacetone, hydroxypyruvic acid, glyceraldehyde, glyceric acid, pyruvic acid, hydroxymalonic acid and lactic acid.

7. The process for producing a compound having a carbonyl group and/or a carboxyl group according to claim 1, wherein the compound having a carbonyl group and/or a carboxyl group is dihydroxyacetone, hydroxyacetone or a mixture of them and the pH is maintained in the range of 7 to 1 in the catalytic oxidation.

8. The process for producing a compound having a carbonyl group and/or a carboxyl group according to claim 1, wherein the compound having a carbonyl group and/or a carboxyl group is dihydroxyacetone, hydroxyacetone or a mixture of them and the catalytic oxidation temperature is −20° to 60° C.

9. The process for producing a compound having a carbonyl group and/or a carboxyl group according to claim 1, wherein the compound having a carbonyl group and/or a carboxyl group is dihydroxyacetone, hydroxyacetone or a mixture of them and the molar ratio of oxygen to the polyhydric alcohol in the catalytic oxidation is 0.25:1 to 30:1.

10. The process for producing a compound having a carbonyl group and/or a carboxyl group according to claim 1, wherein the compound having a carbonyl group and/or a carboxyl group is at least one compound selected from the group consisting of glyceric acid, lactic acid and hydroxymalonic acid, and in the catalytic oxidation, the pH is maintained in the range of 1 to 7.5 when the catalytic component contains platinum or in the range of 7.5 to 13 when the catalytic component does not contain platinum.

11. The process for producing a compound having a carbonyl group and/or a carboxyl group according to claim 1, wherein the compound having a carbonyl group and/or a carboxyl group is at least one compound selected from the group consisting of glyceric acid, lactic acid and hydroxymalonic acid and the catalytic oxidation temperature is 0° to 80° C.

12. The process for producing a compound having a carbonyl group and/or a carboxyl group according to claim 1, wherein the compound having a carbonyl group and/or a carboxyl group is at least one compound selected from the group consisting of glyceric acid, lactic acid and hydroxymalonic acid and the molar ratio of oxygen to the polyhydric alcohol is 0.5:1 to 20:1 in the catalytic oxidation.

13. The process for producing a compound having a carbonyl group and/or a carboxyl group according to claim 1, wherein a fixed bed reactor having a reaction column containing the supported catalyst fixed therein in which liquid and gas phases are to be continuously flowed over the catalyst is used, and oxygen gas or an oxygen-containing gas and the polyhydric alcohol are flowed in molar ratio of oxygen to the polyhydric alcohol of 0.1:1 to 100:1.

14. The process for producing a compound having a carbonyl group and/or a carboxyl group according to claim 13, wherein the oxygen-containing gas is air or a gaseous mixture of nitrogen and oxygen.

15. The process for producing a compound having a carbonyl group and/or a carboxyl group according to claim 13, wherein the support is at least one member selected from the group consisting of active carbon, carbon black, silica, alumina, silica/alumina, zeolite, molecular sieve and asbestos.

16. The process for producing a compound having a carbonyl group and/or a carboxyl group according to claim 13, wherein the support is active carbon and/or carbon black.

17. The process for producing a compound having a carbonyl group and/or a carboxyl group according to claim 13, wherein the polyhydric alcohol is glycerol and/or 1,2-propylene glycol.

18. The process for producing a compound having a carbonyl group and/or a carboxyl group according to claim 13, wherein the compound having a carbonyl group and/or a carboxyl group is at least one compound selected from the group consisting of dihydroxyacetone, hydroxyacetone, hydroxypyruvic acid, glyceraldehyde, glyceric acid, pyruvic acid, hydroxymalonic acid and lactic acid.

19. The process for producing a compound having a carbonyl group and/or a carboxyl group according to claim 13, wherein the compound having a carbonyl group and/or a carboxyl group is dihydroxyacetone, hydroxyacetone or a mixture of them and the pH of the reaction mixture at the outlet of the reaction column is maintained at 7 to 1.

20. The process for producing a compound having a carbonyl group and/or a carboxyl group according to claim 13, wherein the compound having a carbonyl group and/or a carboxyl group is dihydroxyacetone, hydroxyacetone or a mixture of them and the catalytic oxidation temperature is −20° to 60° C.

21. The process for producing a compound having a carbonyl group and/or a carboxyl group according to claim 13, wherein the compound having a carbonyl group and/or a carboxyl group is dihydroxyacetone, hydroxyacetone or a mixture of them and the molar ratio of oxygen to the polyhydric alcohol in the catalytic oxidation is 0.25:1 to 30:1.

* * * * *